US008491874B2

(12) United States Patent
Creamer et al.

(10) Patent No.: US 8,491,874 B2
(45) Date of Patent: Jul. 23, 2013

(54) PERMANGANATE CONTAINING WHITENING COMPOSITIONS AND METHODS OF THEIR USE

(75) Inventors: Charles E. Creamer, Ridgefield, CT (US); Vincent A. Paradiso, New Milford, CT (US)

(73) Assignee: Millennium Dental International, Inc., Brookfield, CT (US)

( * ) Notice: Subject to any disclaimer, the term of this patent is extended or adjusted under 35 U.S.C. 154(b) by 0 days.

(21) Appl. No.: 13/590,579

(22) Filed: Aug. 21, 2012

(65) Prior Publication Data

US 2012/0315227 A1 Dec. 13, 2012

Related U.S. Application Data

(63) Continuation of application No. 11/661,065, filed as application No. PCT/US2005/029926 on Aug. 23, 2005, now Pat. No. 8,277,783.

(60) Provisional application No. 60/604,115, filed on Aug. 24, 2004.

(51) Int. Cl.
*A61K 8/22* (2006.01)
*A61K 8/362* (2006.01)
*A61K 8/25* (2006.01)
*A61K 8/24* (2006.01)
*A61K 8/36* (2006.01)
*A61Q 11/00* (2006.01)

(52) U.S. Cl.
USPC .................................. 424/53; 424/49; 424/52

(58) Field of Classification Search
USPC .................. 424/53, 401; 433/217.1; 510/303, 510/310
See application file for complete search history.

(56) References Cited

U.S. PATENT DOCUMENTS

| 636,986 | A | 11/1899 | Heinen |
| 2,634,577 | A | 4/1953 | Halford et al. |
| 3,035,883 | A | 5/1962 | Heinze et al. |
| 3,657,413 | A | 4/1972 | Rosenthal |
| 4,032,627 | A | 6/1977 | Suchan et al. |
| 4,576,609 | A | 3/1986 | Hageman et al. |
| 4,728,455 | A * | 3/1988 | Rerek ............................ 510/303 |
| 5,425,953 | A | 6/1995 | Sintov et al. |
| 5,624,906 | A | 4/1997 | Vermeer |
| 6,447,757 | B1 | 9/2002 | Orlowski et al. |
| 6,479,037 | B1 | 11/2002 | Montgomery |
| 6,818,682 | B2 | 11/2004 | Fasafi et al. |
| 2002/0018754 | A1 | 2/2002 | Sagel et al. |
| 2004/0185013 | A1 | 9/2004 | Burgio et al. |
| 2008/0234166 | A1* | 9/2008 | Martin et al. .................. 510/310 |
| 2008/0299520 | A1* | 12/2008 | Ali et al. ..................... 433/217.1 |
| 2009/0035230 | A1* | 2/2009 | Creamer et al. ................. 424/53 |

FOREIGN PATENT DOCUMENTS

| EP | 1 192 933 | 3/2002 |
| FR | 2 828 232 | 2/2003 |
| GB | 294586 | 7/1928 |
| GB | 490384 | 8/1938 |
| JP | 60-13707 | 1/1985 |

OTHER PUBLICATIONS

Buckly, Ph.G., D.D.S., J.P., "Modern Dental Materia Medica, Pharmacology and Therapeutics Including The Application of Drugs and Remedies in the Treatment of Disease", P. Blakiston's Son & Co., The Maple Press, Fourth Edition, Apr. 1917, p. 70.
European Search Report from EP 05 79 1247 dated Feb. 20, 2009.
Hattab, BDS, PhD., Faiez N., et. al., "Dental Discoloration: An Overview", Journal of Esthetic Dentistry, vol. 11, No. 6, 1999, pp. 291-310.
International Search Report from PCT/US2005/029926 dated Feb. 8, 2006.
Popular Science, vol. 142, No. 3, Mar. 1943, pp. 117-118.
Ward, Marcus L., et al. eds., "Discolored Teeth and Their Treatment", The American Text-Book of Operative Dentistry, 5th ed., Lea and Fefiber, 1920, Chapter XI by Herman Prinz, M.D., D.D.S, pp. 467-497.
Ward, Marcus L., et al., "Pyorrhea Alveolaris", The American Text-Book of Operative Dentistry, 5th ed., Lea and Fefiber, 1920; Chapter XIII, p. 578.

* cited by examiner

*Primary Examiner* — Walter Webb
(74) *Attorney, Agent, or Firm* — Honigman Miller Schwartz and Cohn LLP; Andrew N. Weber; Jonathan P. O'Brien

(57) ABSTRACT

In general, the invention provides a fast-acting, whitening composition containing permanganate. Particular alkali-metal or alkaline-earth metal salts of permanganate; hydrogen peroxide; or an alkali or alkaline-earth metal peroxide; and an acid.

10 Claims, 1 Drawing Sheet

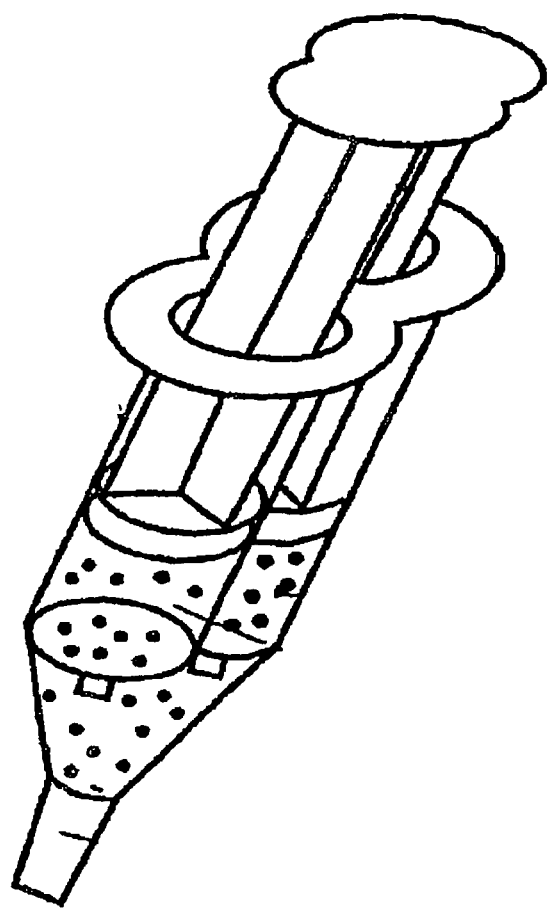

PERMANGANATE CONTAINING WHITENING COMPOSITIONS AND METHODS OF THEIR USE

This continuation application claims the benefit of U.S. application Ser. No. 11/661,065, filed Feb. 22, 2007, which claims the benefit of PCT Application Serial No. PCT/US2005/029926, filed Aug. 23, 2005, which claims the benefit of U.S. Application No. 60/604,115, which was filed on Aug. 24, 2004. The entire contents of the aforementioned references are incorporated herein by reference.

TECHNICAL FIELD

In general, the present invention relates to dental whitening compositions. In particular, the invention provides permanganate containing compositions that are used as dental whitening agents.

BACKGROUND

White teeth are considered cosmetically desirable. Unfortunately, teeth become discolored during the normal aging process and when exposed to substances such as tobacco, certain chromogens in foods and beverages, such as tea and coffee, and medicinal substances.

The components of teeth that acquire stains are enamel, dentin, and pellicle. Tooth discoloration results from both extrinsic and intrinsic staining. Extrinsic staining of the tooth surface arises as a result of the accumulation of various chromogenic substances (in addition to chromogen precursors, which are initially colorless, but later chemically convert to chromogens) within the pellicle. This type of staining may be reduced by removing the pellicle layer containing the adherent chromogens, such as with mechanical abrasion. As the pellicle layer reforms in the mouth, extrinsic staining may reoccur and require subsequent mechanical removal. Intrinsic staining occurs as a result of chromogenic substances derived from sources within the tooth, or from stains derived from external sources that penetrate into the tooth, particularly the enamel layer. Intrinsic staining is not amenable to removal by mechanical methods of tooth cleaning. This type of staining may be reduced by using chemical agents that oxidize or solubilize chromogens in the enamel layer.

Tooth-whitening compositions generally fall into two categories: (1) liquids, powders, gels, or pastes that mechanically or superfluidly abrade or erode stains located in the pellicle layer; and (2) liquids, gels, or pastes that chemically oxidize the stains in the pellicle and in the enamel or dentin components. Tooth-whitening compositions may be used by professionals in dental offices and by consumers in residential settings. The majority of professionals use mechanical abrasion to remove stains and tooth-whitening compositions that oxidate and remove dental stains. Current tooth-whitening compositions that utilize oxidizers are applied to the teeth for a period of time often greater than 30 minutes, and sometimes as long as 8 to 12 hours per day for 1 to 2 weeks in order to produce noticeable stain reduction. The slow rate of whitening is in large part the consequence of formulations that are developed to maintain stability of the oxidizing composition prior to use. These oxidizing compositions typically contain an oxidizing agent, such as hydrogen peroxide or a hydrogen peroxide precursor, e.g., carbamide peroxide, sodium peroxide, or calcium peroxide, which is mixed with an anhydrous or low-water content, hygroscopic viscous carrier containing glycerin and/or propylene glycol and/or polyethylene glycol. Some oxidizing compositions include up to about 38% by weight of hydrogen peroxide.

Prolonged exposure of teeth to current whitening compositions has a number adverse effects. These include: 1) sensitizing the tooth to heat, cold, and overly sweet substances possibly due to the use of peroxides and hygroscopic viscous carriers, 2) irritating mucous membranes with high concentrations of peroxide, 3) solubilizing calcium components from the enamel layer at pH level less than 5.5 with associated transient demineralization, 4) penetrating the intact enamel and dentin by the whitening agents, so as to reach the pulp chamber of a vital tooth thereby risking minor penetration of pulpal tissues, and 5) forming reactive species that have been implicated in the formation of dysplastic cells.

There is a need for whitening teeth while avoiding the adverse effects usually associated with prolonged exposure to common tooth whitening compositions.

SUMMARY OF THE INVENTION

In general, the invention provides a fast-acting, whitening composition containing permanganate.

In one aspect the invention provides a composition including a compound of the formula $R_1(MnO_4)_n$, or mixtures thereof, wherein $R_1$ is H, an alkali-metal, or an alkaline earth metal, and n is 1 when $R_1$ is H or an alkali-metal and 2 when $R_1$ is an alkaline earth metal and an alkali metal peroxide, an alkaline earth metal peroxide, or mixtures thereof.

Embodiments of this aspect may include one or more of the following. The composition includes between about 0.005 to about 3.0 percent by weight of the $R_1(MnO_4)_n$ compound. The composition includes between about 1.0 to about 4.0 percent by weight of the alkali-metal peroxide or the alkaline earth metal peroxide. $R_1$ is potassium, sodium, or calcium. The alkali-metal peroxide or an alkaline earth metal peroxide is calcium peroxide or sodium peroxide. The composition further includes a thickening agent such as pyrogenic silica, precipitated silica, or silicate thickening agents.

In another aspect, the invention provides a container including a housing having a first compartment and a second compartment. The first compartment includes a first composition having a compound of the formula $R_1(MnO_4)_n$, or mixtures thereof, in which $R_1$ is H or an alkali-metal, or an alkaline earth metal, and n is 1 when $R_1$ is an alkali-metal and 2 when $R_1$ is an alkaline earth metal. The second compartment includes a second composition having an acid.

Embodiments of this aspect of the invention may include one or more of the following. The acid is hydrochloric acid, phosphoric acid, acetic acid, sulfuric acid, nitric acid, proprionic acid, maleic acid, or citric acid. The second composition has a pH less than about 7.5. The first composition further includes an alkali-metal peroxide, an alkaline earth metal peroxide, such as calcium peroxide and sodium peroxide, or mixtures thereof. The first composition includes between about 1.0 to about 4.0 percent by weight of the alkali-metal peroxide or the alkaline earth metal peroxide. The second composition further comprises a hydrogen peroxide, urea peroxide, an alkali-metal peroxide, an alkaline earth metal peroxide, or mixtures thereof. The second composition includes between about 1.0 to about 4.0 percent by weight of hydrogen peroxide, urea peroxide, an alkali-metal peroxide, or an alkaline earth metal peroxide. The first composition further includes a thickening agent, such as pyrogenic silica, precipitated silica, or silicate thickening agents. The first composition includes between about 0.005 to about 3.0 percent by weight of the $R_1(MnO_4)_n$ compound. $R_1$ is potassium, sodium, or calcium.

In another aspect, the invention provides a container including a housing including a first compartment and a second compartment. The first compartment includes a first composition having a compound of the formula $R_1(MnO_4)_n$, or mixtures thereof, in which $R_1$ is H, an alkali-metal, or an alkaline earth metal, and n is 1 when $R_1$ is H or an alkali-metal and 2 when $R_1$ is an alkaline earth metal. The second compartment includes a second composition having a peroxygen compound, or mixtures thereof, in which the peroxygen compound is hydrogen peroxide, urea peroxide, an alkali-metal peroxide, or an alkaline earth metal peroxide.

Embodiments of this aspect of the invention may include one or more of the following. The second composition includes between about 1.0 to about 4.0 percent by weight of the peroxygen compound. The alkali-metal peroxide and the alkaline-earth metal peroxide are selected from calcium peroxide, sodium peroxide. The first composition further comprises an acid, such as hydrochloric acid, phosphoric acid, acetic acid, sulfuric acid, nitric acid, proprionic acid, maleic acid, or citric acid. The first composition has a pH between about 4.0 and about 7.5. The first composition further includes a thickening agent, such as pyrogenic silica, precipitated silica, or silicate thickening agents. The first composition includes between about 0.005 to about 3.0 percent by weight of the $R_1(MnO_4)_n$ compound. $R_1$ is H, potassium, sodium, or calcium.

In another aspect, the invention provides a method of whitening a tooth that includes applying to the tooth a compound of the formula $R_1(MnO_4)_n$, or mixtures thereof, wherein $R_1$ is H, an alkali-metal, or an alkaline earth metal, and n is 1 when $R_1$ is H or an alkali-metal and 2 when $R_1$ is an alkaline earth metal; and a peroxygen compound, or mixtures thereof, wherein the peroxygen compound is hydrogen peroxide, urea peroxide, an alkali-metal peroxide, or an alkaline earth metal peroxide. The method may further include the step of applying an acid, such as hydrochloric acid, phosphoric acid, acetic acid, sulfuric acid, nitric acid, proprionic acid, maleic acid, or citric acid, to the tooth. Each of the $R_1(MnO_4)_n$ compound, the peroxygen compound, and the acid may be separately or simultaneously applied to the tooth. For instance, the $R_1(MnO_4)_n$ compound and the acid may be simultaneously applied to the tooth. Alternatively, the peroxygen compound and the acid may be simultaneously applied to the tooth. Still further, the $R_1(MnO_4)_n$ compound and the peroxygen compound may be simultaneously applied to the tooth. The peroxygen compound may be applied to the tooth after the $R_1(MnO_4)_n$ compound is applied to the tooth. The peroxygen compound and the acid may be applied as aqueous solutions. The pH of the combined solution containing the $R_1(MnO_4)_n$ compound, the peroxygen compound, and the acid is between about 4.0 and about 7.5. The peroxygen compound may be hydrogen peroxide, urea peroxide, or an alkali-metal peroxide or an alkaline earth metal peroxide, such as such as calcium peroxide or sodium peroxide. $R_1$ is potassium, sodium, or calcium.

Advantageously, the composition and methods of this invention provide a whitening composition that whitens teeth at a substantially faster rate than current peroxide based whitening compositions thereby minimizing problems, such as tooth sensitization, irritation, demineralization, pulpal tissue penetration, and formation or reactive species which may form dysplastic cells, that result from prolonged exposure to peroxide and/or hygroscopic viscous carriers. Additionally; the whitening composition exhibits a visual signal, such as by turning from a purple-violet color to colorless, when the oxidation process for that application of the whitening composition is complete. Surprisingly, the composition and methods of this invention produce whiter teeth even though the whitening composition includes the highly chromatic permanganate.

Other features and advantages of the invention will be apparent from the description and the claims which follow.

BRIEF DESCRIPTION OF THE DRAWINGS

FIG. 1 shows a dual barreled syringe that may be useful in dispensing components of the whitening composition.

DETAILED DESCRIPTION OF THE INVENTION

The whitening composition of this invention includes three main components, an oxidizing agent, a reducing agent, and an acidifying agent.

The oxidizing agent includes permanganic acid, permanganate salts, or mixtures thereof. For instance, the oxidizing agent may be permanganic acid, $HMnO_4$, an alkali-metal salt, or an alkaline-earth metal salt of permanganic acid. Examples of suitable oxidizing agents include, but are not limited to, $HMnO_4$, $KMnO_4$, $NaMnO_4$, and $Ca(MnO_4)_2$. The oxidizing agent may be formed as a solution, paste, or gel, and contains between about 0.005 to about 3.0 percent by weight (such as between about 0.01 to about 2.0 percent by weight, between about 0.1 to about 1.0 percent by weight, or between about 0.2 to about 0.6 weight percent) of the permanganic acid or mixtures thereof. In some embodiments, the oxidizing agent can contain about 30 percent by weight, or less of the permanganic acid or mixtures thereof.

The reducing agent includes hydrogen peroxide or precursors of hydrogen peroxide. Precursors of hydrogen peroxide are compounds that can be used to form hydrogen peroxide. Examples of suitable reducing agents include, but are not limited to, hydrogen peroxide, urea peroxide, and alkali-metal peroxides, such as sodium peroxide, and alkaline-earth metal peroxides, such as calcium peroxide. The reducing agent may be formed as a solution, paste, or gel, and contains between about 1.0 to about 4.0 percent by weight (such as between about 2.0 to about 3.5 percent by weight or between about 2.5 to about 3.0 percent by weight) of hydrogen peroxide, precursors of hydrogen peroxide or mixtures thereof. In some embodiments, the reducing agent can contain about 30 percent by weight, or less of hydrogen peroxide, precursors of hydrogen peroxide or mixtures thereof.

The acidifying agent includes any inorganic acid, organic acid, or mixtures thereof. Examples of suitable acidifying agents include, but are not limited to, hydrochloric acid, phosphoric acid, acetic acid, sulfuric acid, nitric acid, proprionic acid, maleic acid, and citric acid. The acidifying agent may be formed as a solution, paste, or gel, and contains between about 0.1 to about 2.0 percent by weight (such as between about 0.5 to about 1.0 percent by weight) of the acid or mixtures thereof.

When forming a gel or paste of the oxidizing agent, reducing agent, or acidifying agent, a thickening agent is mixed into a permanganate solution, a hydrogen peroxide solution, a solution of precursors of hydrogen peroxide, or an acid solution in an amount to achieve the desired consistency. Examples of thickening agents include, but are not limited to, pyrogenic silica, precipitated silica, or silicate thickening agents such as magnesium silicate. Other thickening agents may be used so long as they do not eliminate the whitening effect of the composition such as by oxidatively reducing the permanganate, oxidizing the hydrogen peroxide or precursors of hydrogen peroxide, or neutralizing the acid.

The whitening composition can be administered by a dental practitioner in a dental office or applied in the home environment by individuals desiring whiter teeth. The whitening composition is applied to the teeth directly such as by painting the solutions onto the teeth with a brush, spraying the solutions onto the teeth with one or more syringes, and soaking the teeth in the solutions, such as with a preformed silicon mouth whitening tray. Silicone mouth whitening trays are available from Henry Schein Company, located at 135 Duryea Road, Melville, N.Y. 11747. Advantageously, the whitening composition exhibits a visual signal, such as by turning from a purple-violet color to colorless when the oxidation process for that application of the whitening composition is complete.

The three components of the whitening composition, e.g., oxidizing agent, reducing agent, and acidifying agent, may be applied sequentially or simultaneously as a single composition. Additionally, as will be described in greater detail below, two of the three components of the whitening composition may be mixed together before application.

In a sequential application, the oxidizing agent is applied to the teeth for between about 0.2 to about 15 minutes (such as between about 0.2 to about 5 minutes). In some embodiments, the oxidizing agent is applied to the teeth for less than about 10 minutes (such as less than about 5 minutes). The exact length of application depends upon the concentration of the permanganic acid and the desired level of whitening. Higher concentrations require less contact time than lower concentrations. Using highly dilute solutions of oxidizing agent such as (less than 0.01% by weight) may require repeated applications of the whitening composition to achieve a desired level of whitening.

After the oxidizing agent has been in contact with the teeth for the desired amount of time, the reducing agent and the acidifying agent are applied, in any order, to the teeth to remove excess permanganate and reduction byproducts. Typically, enough acidifying agent is added so that a mixture of the three components of the whitening composition has a pH between about 4.0 to about 7.5 (such as between about 4.0 to about 5.0). The time required to remove all of the permanganate and reductive byproducts ranges from between about 30 seconds to about 10 minutes (such as between about 1 to about 5 minutes). At contact times less than about 10 minutes, the compounds of the reducing agent, i.e., hydrogen peroxide or precursors of hydrogen peroxide, produce no oxidative whitening upon visual inspection. The exact length time for applying the reducing agent and the acidifying agent depends upon the concentration of the permanganate and the concentration of reducing agent.

In a simultaneous application, the oxidizing agent, reducing agent, and acidifying agent are applied simultaneously as a single composition. For instance, the three components of the whitening composition are mixed and then applied to the teeth by brush, syringe, or dental tray. Alternatively, each of the three components are separately contained in one of three barrels of a three-barreled syringe and then mixed together as they exit the syringe tip. Multiple barreled syringes may be formed by connecting the end of each single syringe to a common tip with, for example, silicone tubing. FIG. 1 shows an illustration of a dual barreled syringe that may be useful in dispensing components of the whitening composition. Multiple barreled syringes are also available from Comprotech, Transcoject, and MixPac. The amount of oxidizing agent, reducing agent, and acidifying agent dispensed by the syringe depends upon the concentration of permanganate, the hydrogen peroxide or precursors of hydrogen peroxide, and the acid. In general, the multi-barreled syringe may contain the oxidizing agent, reducing agent, and acidifying agent at any concentration, even above or below those specific concentrations listed above. In some embodiments, the concentrations of the oxidizing agent, reducing agent, and acidifying agent in the multi-barreled syringe are stoichiometrically adjusted such that the solution eluting from the syringe primarily contains $HMnO_4$. In other embodiments, the syringe may dispense equal amounts of a oxidizing agent containing 1% by weight of permanganate and of a reducing agent containing 3% by weight of hydrogen peroxide or a precursor of hydrogen peroxide. Typically, enough acidifying agent is dispensed from the syringe so that the mixture of the three components of the whitening composition has a pH between about 4.0 to about 7.5 (such as between about 4.0 to about 5.0).

In other embodiments, two components of the whitening composition are mixed together before being applied to the teeth, e.g., pre-mixed. For instance, the oxidizing agent and the acidifying agent are pre-mixed and then applied to the teeth. After between about 0.2 to about 15 minutes (such as between about 0.2 to about 10 minutes), the reducing agent is applied to the teeth to remove any residual permanganate and reduction byproducts. Alternatively, the oxidizing agent is applied to the teeth and a pre-mixture of the reducing agent and the acidifying agent is applied to the teeth to remove residual permanganate and reduction byproducts. In either scenario, the two components may be pre-mixed immediately or several days, weeks, or months before application. The two pre-mixed components may be stored in a container such as in one barrel of a duel-barreled syringe. The other barrel of the syringe could contain the remaining component of the whitening composition.

In another embodiment, the oxidizing agent and the reducing agent are mixed together before being applied to the teeth. The acidifying agent is added to the teeth after about 0.2 to about 10 minutes (such as between about 0.2 to about 5 minutes). The oxidizing agent and the reducing agent may be mixed immediately before application. Alternatively, when the reducing agent is an alkali metal or alkaline-earth metal peroxide, the oxidizing agent and the reducing agent may be mixed together several days, weeks, or months before application. The two pre-mixed components may be stored in a container such as in one barrel of a duel-barreled syringe. The other barrel of the syringe could contain the acidifying agent.

Other embodiments are with the following Examples.

In each of the following examples, the whiteness of a tooth was determined by visual comparison of the tooth with a Vita Shade Guide. Vita Shade Guides are available from VITA ZAHNFABRIK, located in Brea, Calif. The Vita Shade Guides provide a whiteness scale used throughout the dental industry. The whiteness of a tooth is determined by visually comparing the tooth with the Vita Shade Guide to determine a whiteness grade. The whiteness shades are given below:

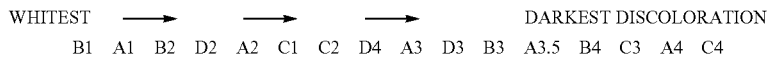

WHITEST ⟶ ⟶ ⟶ DARKEST DISCOLORATION
B1 A1 B2 D2 A2 C1 C2 D4 A3 D3 B3 A3.5 B4 C3 A4 C4

EXAMPLE 1

A 1% by weight solution of potassium permanganate was prepared by dissolving 0.5 grams of potassium permanganate (Sigma-Aldrich, Milwaukee, Wis.) in 49.5 grams of distilled water. The pH of this solution was determined to be 7.2. A thin layer of this solution was painted on a severely stained human tooth. The stained tooth whiteness was darker than any specimen on a Vita Shade Guide.

The painted surface of the tooth had a reddish purple color characteristic of solutions containing permanganate ion. After five minutes of treatment, the tooth was washed with a solution of 3% by weight hydrogen peroxide (Sigma-Aldrich, Milwaukee, Wis.) which was acidified to a pH of 5.0 using citric acid (Sigma-Aldrich, Milwaukee, Wis.). The permanganate color disappeared in a matter of seconds. The Vita Shade Guide rating of the tooth was determined to be A4.

The tooth was re-treated with the potassium permanganate solution for an additional five minutes, and then washed with the hydrogen peroxide solution. Again, the permanganate color disappeared almost instantly. The tooth color was determined with a Vita Shade Guide to be D3. The whiteness change from A4 to D3 represents a whitening of 5 shades. After a third five minute treatment with the potassium permanganate solution, followed by washing with the peroxide solution, the Vita Shade Guide rating was found to be A2. The whiteness change from D3 to A2 represents a whitening of another 5 shades. A forth 5 minute treatment resulted in a Vita Shade Guide rating of A1. The whiteness change from A2 to A1 represents a whitening of 3 shades.

EXAMPLE 2

A 0.5% by weight solution of calcium permanganate was prepared by adding 0.25 grams of calcium permanganate (made from 0.1 moles $CaCl_2$ (aq)+0.2 $K(MnO_4)_2$ (aq)) to 49.75 grams of distilled water. The pH of this solution was found to be 7.1. This solution was painted on a human tooth having a Vita Shade Guide rating of D3. After five minutes of treatment the tooth was washed with the acidified solution of hydrogen peroxide used in Example 1. The Vita Shade Guide rating of the tooth was determined to be C1. The whiteness change from D3 to C1 represents a whitening of 4 shades. After 5 minutes of additional treatment, followed by washing with the hydrogen peroxide solution, the tooth had a Vita Shade Guide rating of D2. The whiteness change from C1 to D2 represents a whitening of 3 shades.

EXAMPLE 3

Example 1 was repeated by treating a human tooth having a Vita Shade Guide rating of A4 with the 1% by weight potassium permanganate solution from Example 1. A 3.0% solution of hydrogen peroxide (Sigma-Aldrich, Milwaukee, Wis.) acidified to a pH of 5.0 with phosphoric acid (Sigma-Aldrich, Milwaukee, Wis.) was used to wash the tooth. After twelve minutes of treatment with the potassium permanganate solution from Example 1 followed by the acidified peroxide wash, the Vita Shade Guide rating of the tooth was found to be A2. The whiteness change from A4 to A2 represents a whitening of 10 shades The tooth was retreated for five minutes with the potassium permanganate solution from Example 1 followed by the acidified peroxide wash. The final Vita Shade Guide rating was found to be A1. The whiteness change from A2 to D1 represents a whitening of 3 shades.

EXAMPLE 4

An aqueous gel containing 1% by weight of potassium permanganate was prepared by adding 0.5 grams of potassium permanganate (Sigma-Aldrich, Milwaukee, Wis.) and 5.0 grams of CAB-O-SIL L-90 (Cabot Corporation, Tuscola II, 61953) to 44.5 grams of distilled water. A 3.0% by weight solution of hydrogen peroxide (Sigma-Aldrich, Milwaukee, Wis.), acidified to a pH of 5.0 with hydrochloric acid (Sigma-Aldrich, Milwaukee, Wis.) was gelled by adding 6 grams of CAB-O-SIL L-90 to 44.0 grams of aqueous solution.

The potassium permanganate gel was spread on the surface of a human tooth having a discoloring darker than specimens on the Vita Shade Guide. The surface color of the tooth was reddish-violet. After 6 minutes of treatment with the potassium permanganate gel, the hydrogen peroxide gel was spread on the tooth. After about two minutes, the color of the tooth was a light yellow. The tooth was washed with distilled water and the tooth color was rated with the Vita Shade Guide as B4, representing a change in whiteness of at least 4 shades. The tooth was re-treated in the same manner for an additional 8 minutes. The Vita Shade Guide color was determined to be C2. The whiteness change from B4 to C2 represents a whitening of 6 shades. After an additional 4 minutes of treatment, the Vita Shade Guide rating of the tooth was found to be between A1 and B1, representing a change in whiteness of at least 5 shades.

EXAMPLE 5

Solution A). A 1% by weight solution of potassium permanganate was prepared by dissolving 0.5 grams of potassium permanganate (Sigma-Aldrich, Milwaukee, Wis.) in 49.5 grams of distilled water. Solution B), a 1.4% by weight of calcium peroxide, was prepared by adding 0.7 grams of calcium peroxide (Sigma-Aldrich, Milwaukee, Wis.) to 49.3 grams of distilled water. Solution C) was prepared by mixing 20 grams of Solution A to 20 grams of Solution B. Solution D), a 1% by weight solution of citric acid (Sigma-Aldrich, Milwaukee, Wis.) was prepared by adding 1 gram of citric acid to 99 grams of distilled water.

A human tooth having a Vita Shade Guide shade of D4 was placed in a 50 cc plastic vial. 6 cc's of Solution C was added to the vial containing the tooth using a plastic hypodermic syringe. 6 cc's of Solution D) was immediately injected into the vial, and the contents were swirled to achieve mixing. The pH of the solution containing the tooth was found to be 4.5. After 5 minutes, the tooth was removed from the vial, rinsed with distilled water. The color of the tooth was determined with the Vita Shade Guide to be C2, representing a change in whiteness of 1 grade.

The tooth was placed back in the vial containing the mixture of Solutions C) and D). After an additional five minutes, the tooth was removed and rinsed with distilled water. Its Vita Shade Guide reading was found to be D2, an improvement of four shades.

The color of the mixture of Solution C) and D) was light yellow after 12 minutes. The tooth was added back to this mixture, and after an additional 5 minutes, it was removed and again rinsed with distilled water. The Vita Shade Guide evaluation was found to be D2, and the solution in which it had been treated was clear. An additional five minutes of treatment produced no further reduction in shade.

This example demonstrates the tooth-whitening efficacy of compositions containing alkali-metal salts of permanganic acid.

EXAMPLE 6

Experiment 1 was repeated using a tooth having a Vita Shade Guide rating of A3.5. After five minutes of treatment, its Vita Shade Guide rating was C1, corresponding to an improvement of 6 shades. Further treatment of the tooth for an additional 5 minutes resulted in a Vita Shade Guide rating of between shade D2 and A2, an additional change of 1 shade. The treating solution was completely clear after 20 minutes.

EXAMPLE 7

The teeth used in Experiments 1 and 2 were re-treated using the exact method used in Experiment 1. After five minutes of treatment, the shade of the tooth used in Experiment 1 was determined to be B2, a further improvement of 1 shade. The shade of the tooth used in Experiment 2 was also determined to be B2 corresponding in change in whiteness of an additional 2 shades. After an additional five minutes of treatment, the tooth used in Experiment 1 was found to have a Vita Shade Guide shade of A1, for an additional improvement of one shade. The solution used to treat this tooth was a very light yellow after this treatment. Within one hour the solution was water-white and crystal clear.

An additional five minutes of treatment resulted in no further improvement in shade of the tooth used in Experiment 2. Again, within one hour the treating solution was water-white and crystal clear.

These experiments demonstrate the whitening efficacy of multiple treatments of tooth-whitening compositions containing alkali-metal salts of permanganic acid.

EXAMPLE 8

A human tooth having a Vita Shade Guide rating of D4 was immersed in 6 cc's of calcium peroxide (made as described in example 2) solution having the composition of Solution B above. 6 cc's of 1% citric acid solution prepared by adding 0.5 grams of citric acid (Sigma-Aldrich, Milwaukee, Wis.) in 49.5 grams of distilled water were added to the mixture. The pH of the acidified solutions was determined to be 4.3.

After five minutes immersion, the tooth was removed from the solution, rinsed with distilled water. The Vita Shade Guide reading was determined and found to be D4.

The tooth was re-immersed in the in the acidified Solution B. After 10 minutes, the tooth was removed and found to have a Vita Shade Guide reading of D4.

The tooth was re-immersed in the acidified Solution B. After 20 minutes, the tooth was removed and tested for shade. The Vita Shade Guide rating was again D4.

The tooth was again re-immersed in the acidified Solution B. After one hour, the Vita Shade Guide rating remained at D4.

This experiment demonstrates that acidified solutions of calcium peroxide, without the necessary alkali-metal salts of permanganic acid, exhibit no visible efficacy in reducing the color of stained teeth.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of whitening a tooth comprising:
applying to the tooth
an oxidizing agent comprising a compound of the formula $R_1(MnO_4)_n$, or mixtures thereof, wherein $R_1$, is H, an alkali-metal, or an alkaline earth metal, and n is 1 when $R_1$ is H or an alkali-metal and 2 when $R_1$ is an alkaline earth metal; and
a reducing agent comprising a peroxygen compound, or mixtures thereof, wherein the peroxygen compound is hydrogen peroxide, urea peroxide, an alkali-metal peroxide, or an alkaline earth metal peroxide;
wherein the oxidizing agent is applied to the tooth for between about 0.2 to about 15 minutes followed by the application of the reducing agent, and the oxidizing agent reacts with the reducing agent on the tooth's surface to whiten the color of the tooth by at least one shade according to the Vita Shade Guide.

2. The method of claim 1, wherein the oxidizing agent further comprises between about 0.005 to about 3.0 percent by weight of the compound of the formula $R_1(MnO_4)_n$.

3. The method of claim 1, wherein the reducing agent further comprises between about 1 to about 4 percent by weight of the peroxygen compound.

4. The method of claim 1, wherein the oxidizing agent, the reducing agent, or both further comprises an acid.

5. The method of claim 4, wherein the acid is selected from hydrochloric acid, phosphoric acid, acetic acid, sulfuric acid, nitric acid, proprionic acid, maleic acid, or citric acid.

6. The method of claim 5, wherein the concentration of the acid in the oxidizing agent, the reducing agent, or both is sufficient to adjust the pH of the mixture of oxidizing agent, the reducing agent, and the acid to between about 4.0 and about 7.5.

7. The method of claim 6, wherein the reducing agent further comprises the acid.

8. The method of claim 1, wherein the oxidizing agent, the reducing agent, or both further comprise a thickening agent.

9. The method of claim 8, wherein the thickening agent comprises pyrogenic silica, precipitated silica, magnesium silicate, or any combination thereof.

10. The method of claim 1, wherein the oxidizing agent is housed separately from the reducing agent prior to the application of the oxidizing agent and the reducing agent to the tooth.

* * * * *